United States Patent [19]
Gehlert et al.

[11] Patent Number: 5,846,973
[45] Date of Patent: Dec. 8, 1998

[54] METHODS OF TREATING PULMONARY HYPERTENSION

[75] Inventors: Donald Richard Gehlert; Mitchell Irvin Steinberg, both of Indianapolis, Ind.

[73] Assignee: Eli Lilly and Company, Indianapolis, Ind.

[21] Appl. No.: 862,709

[22] Filed: May 23, 1997

Related U.S. Application Data

[60] Provisional application No. 60/018,266 May 24, 1996.
[51] Int. Cl.$^6$ .................. A61K 31/495; A61K 31/50; A61K 31/445; A61K 31/405; A61K 31/40
[52] U.S. Cl. .................. 514/249; 514/316; 514/327; 514/415; 514/419
[58] Field of Search .................. 514/249, 316, 514/327, 415, 419

[56] References Cited

U.S. PATENT DOCUMENTS

| | | | |
|---|---|---|---|
| 5,328,927 | 7/1994 | Lewis et al. | 514/415 |
| 5,331,089 | 7/1994 | Curtis et al. | 530/317 |
| 5,344,830 | 9/1994 | Mills et al. | 514/235.8 |
| 5,360,820 | 11/1994 | Hagan et al. | 514/559 |
| 5,491,140 | 2/1996 | Bruns, Jr. et al. | 514/212 |

*Primary Examiner*—Kimberly Jordan
*Attorney, Agent, or Firm*—Paul J. Gaylo; David E. Boone

[57] ABSTRACT

This invention provides methods of inhibiting pulmonary hypertensive disease which comprise administering to a mammal in need thereof a compound having activity as a tachykinin receptor antagonist.

2 Claims, No Drawings

METHODS OF TREATING PULMONARY HYPERTENSION

PRIORITY CLAIM

This application claims the benefit of United States Provisional Patent application Ser. No. 60/018,266, filed May 24, 1996.

BACKGROUND OF THE INVENTION

Tachykinins are a family of peptides which share a common amidated carboxy terminal sequence. Substance P was the first peptide of this family to be isolated, although its purification and the determination of its primary sequence did not occur until the early 1970's.

Between 1983 and 1984 several groups reported the isolation of two novel mammalian tachykinins, now termed neurokinin A (also known as substance K, neuromedin L, and neurokinin α), and neurokinin B (also known as neuromedin K and neurokinin β). See, J. E. Maggio, *Peptides*, 6 (Supplement 3):237–243 (1985) for a review of these discoveries.

Tachykinins are widely distributed in both the central and peripheral nervous systems, are released from nerves, and exert a variety of biological actions, which, in most cases, depend upon activation of specific receptors expressed on the membrane of target cells. Tachykinins are also produced by a number of non-neural tissues.

The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

Tachykinins play a major role in mediating the sensation and transmission of pain or nociception, especially migraine headaches. see e.g., S. L. Shepheard, et al., *British Journal of Pharmacology*, 108:11–20 (1993); S. M. Moussaoui, et al., *European Journal of Pharmacology*, 238:421–424 (1993); and W. S. Lee, et al., *British Journal of Pharmacology*, 112:920–924 (1994).

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instability.

Recent publications have described novel classes of non-peptidyl tachykinin receptor antagonists which generally have greater oral bioavailability and metabolic stability than the earlier classes of tachykinin receptor antagonists. Examples of such newer non-peptidyl tachykinin receptor antagonists are found in U.S. Pat. No. 5,491,140, issued Feb. 13, 1996; U.S. Pat. No. 5,328,927, issued Jul. 12, 1994; U.S. Pat. No. 5,360,820, issued Nov. 1, 1994; U.S. Pat. No. 5,344,830, issued Sep. 6, 1994; U.S. Pat. No. 5,331,089, issued Jul. 19, 1994; European Patent Publication 591,040 A1, published Apr. 6, 1994; Patent Cooperation Treaty publication WO 94/01402, published Jan. 20, 1994; Patent Cooperation Treaty publication WO 94/04494, published Mar. 3, 1994; Patent Cooperation Treaty publication WO 93/011609, published Jan. 21, 1993; Canadian Patent Application 2154116, published Jan. 23, 1996; European Patent Publication 693,489, published Jan. 24, 1996; and Canadian Patent Application 2151116, published Dec. 11, 1995.

Patent Cooperation Treaty Patent Publication WO 96/11000, published Apr. 18, 1996 and European Patent Publication EP 705,600, published Apr. 10, 1996, describe a synergistic effect on the combination of a serotonin agonist and a tachykinin receptor antagonist in treating migraine. U.S. patent application Ser. No. 08/387,056, filed Feb. 10, 1995, describes a synergistic effect on the combination of a serotonin agonist and a tachykinin receptor antagonist in treating a variety of psychiatric disorders. U.S. patent application Ser. No. 08/408,238, filed Mar. 22, 1995, describes a synergistic effect on the combination of a serotonin agonist and a tachykinin receptor antagonist in treating a variety of types of pain and nociception. U.S. patent application Ser. No. 60/000074, filed Jun. 8, 1995, describes a synergistic effect on the combination of a serotonin agonist and a tachykinin receptor antagonist in treating the common cold or allergic rhinitis.

European Patent Application 0 577 394, published Jan. 5, 1994, teaches a series of morpholinyl and thiomorpholinyl tachykinin receptor antagonists. Patent Cooperation Treaty Patent Application WO 95/18124, published Jul. 6, 1995, teaches another series of substituted morpholines for use as tachykinin receptor antagonists. None of these references, nor any combination of them, teach the tachykinin receptor antagonists of the present invention.

Pulmonary hypertension represents a serious, life threatening spectrum of diseases of multiple etiology. These include congenital abnormalities of the lung, thorax and diaphragm, congenital or acquired valvular or myocardial disease, obstructive lung disease, and can be a complication of autoimmune diseases, vasculitis and collagen based diseases (Rubin, *Chest*. 104: 236, 1993). Patients with pulmonary hypertension frequently present with symptoms including dyspnea, fatigue, syncope, and chest pain, and have increased pulmonary artery pressure and demonstrate prominence of the main pulmonary artery, hilar vessel enlargement and decreased peripheral vessels on chest radiographs Rich, *Ann. Internal. Med.*, 107: 216, 1987).

While pulmonary hypertension has multiple etiologies, primary pulmonary hypertension appears to involve an autoimmune component and has been reported as a complication in patients with mixed connective tissue disease, rheumatoid arthritis, Sjogren's syndrome, systemic sclerosis and lupus (Sato, *Hum. Path.*, 24: 199, 1993). Primary pulmonary hypertension occurs in females 1.7 times more frequently than males with the greatest predominance between the third and fourth decades of life (Rich, *Ann. Internal. Med.*, 107: 216, 1987). The increased incidence of primary pulmonary hypertension in women of child bearing age as well as the clinical observations that the disease can be exacerbated by pregnancy and oral contraceptives (Miller, *Ann. Rheum. Dis.* 46: 159, 1987; and cited in Farhat et al., *J PET*, 261: 686, 1992) suggests a role for estrogen in the disease process. To this extent, Farhat et al. have demonstrated that estradiol potentiates the vasopressor response to a thromboxane mimetic in perfused rat lungs (*J PET*, 261: 686, 1992). However, the role of estrogen in pulmonary hypertension is complex and may be dependent on the etiology of the disease process. In a rat model of pulmonary hypertension induced by injection of monocrotaline pyrrole (Reindel, *Tox. Appl. Pharm.*, 106: 179, 1990)

progressive pulmonary hypertension, right ventricular hypertrophy and interstitial edema around the large airways and blood vessels becomes apparent, similar to the pathology observed in man. Estradiol treatment decreased right ventricular hypertrophy and prevented interstitial edema in this model (Farhat et al., *Br. J. Pharm.*, 110: 719, 1993) as well as attenuating the hypoxic vasoconstrictive response in isolated sheep lungs (Gordon et al., *J. Appl. Physiol.*, 61: 2116, 1986).

Current therapy for pulmonary hypertension is inadequate and is largely dependent on the use of vasodilators, diuretics, and anticoagulants (Rubin, *Drugs*, 43: 37, 1992; Palevsky, *JAMA*, 265:1014, 1991). Vasodilators are effective in only a small subpopulation of patients with primary pulmonary hypertension and is complicated by systemic hypotensive responses. Prostacyclin infusion and high dose calcium channel blockers are also being used with limited efficacy. Heart-lung and single lung transplantation have been used on patients which do not respond to vasodilator therapy, however, due to surgical morbidity and mortality, this approach is usually limited to those patients who continue to deteriorate despite aggressive therapy at centers experienced in management of this disease. Patients frequently die of right heart failure and those individuals which have signs of right heart failure have a mean survival of 6–12 months (Rubin, *Drugs*, 43: 37, 1992).

Therefore, pulmonary hypertensive diseases are characterized by inadequate therapies, necessity of organ transplantation and poor prognosis, and a need exists for new therapies.

SUMMARY OF THE INVENTION

This invention provides methods of inhibiting pulmonary hypertensive disease in a mammal which comprise administering to a mammal in need thereof an effective amount of a compound having activity as a tachykinin receptor antagonist.

DETAILED DESCRIPTION AND PREFERRED EMBODIMENTS

The terms and abbreviations used in the instant preparations and examples have their normal meanings unless otherwise designated. For example "°C." refers to degrees Celsius; "N" refers to normal or normality; "mmol" refers to millimole or millimoles; "g" refers to gram or grams; "ml" means milliliter or milliliters; "L" means liter or liters; "M" refers to molar or molarity; "MS" refers to mass spectrometry; "IR" refers to infrared spectroscopy; and "NMR" refers to nuclear magnetic resonance spectroscopy.

The term "inhibit" includes its generally accepted meaning which includes prohibiting, preventing, restraining, and slowing, stopping or reversing progression, severity or a resultant symptom. As such, the present method includes both medical therapeutic and/or prophylactic administration, as appropriate.

Pulmonary hypertensive diseases include all conditions characterized by an increase in the blood pressure within the blood vessels supplying the lungs and can increase the complications associated with pulmonary embolism, heart failure, valvular disease, chronic lung diseases and autoimmunity.

The methods of the present invention employ various tachykinin receptors. In recent publications many different groups of non-peptidyl tachykinin receptor antagonists have been described. The present invention, however, is not limited to any one of the specific compound or class of compound. The present invention encompasses any compound effective as a tachykinin receptor antagonist.

Patent Cooperation Treaty publication WO 94/01402, published Jan. 20, 1994, describes a series of compounds best typified by the following compound.

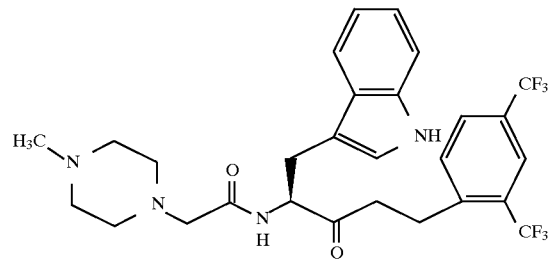

European Patent Publication 591,040 A1, published Apr. 6, 1994 describes a series of compounds typified by the following compound:

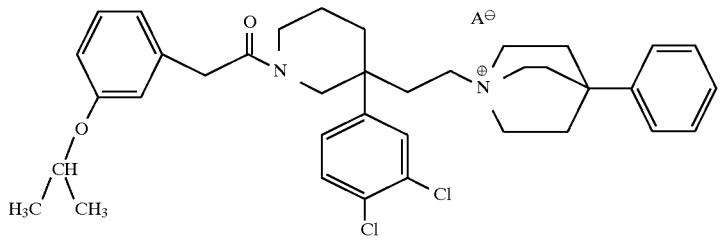

where $A^{\ominus}$ is a pharmaceutically acceptable anion.

Patent Cooperation Treaty publication WO 94/04494, published Mar. 3, 1994, describes a series of compounds typified by the following compound.

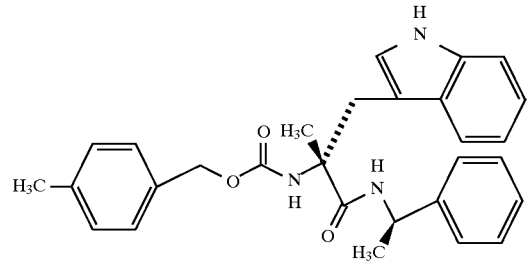

Patent Cooperation Treaty publication WO 93/01169, published Jan. 21, 1993, describes a series of compounds typified by the following compound.

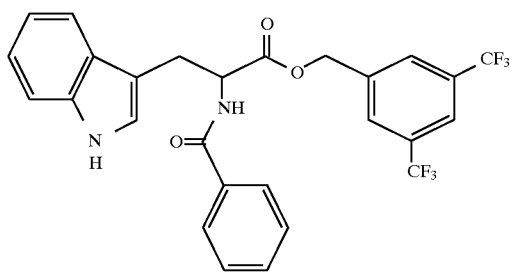

Another group of tachykinin receptor antagonists is characterized by the compound of the formula:

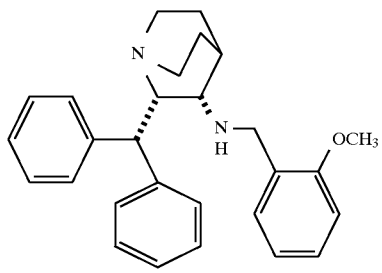

having the designation (±)-CP 96345. These compounds and their syntheses are described in E. J. Warawa, et al., *Journal of Medicinal Chemistry*, 18:357 (1975).

Yet another group of tachykinin receptor antagonists is characterized by the compound of the formula:

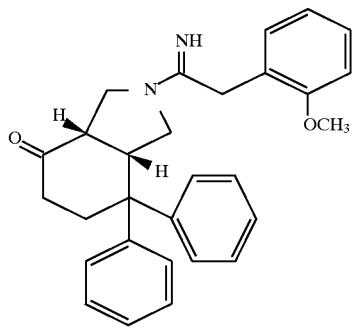

having the designation RP 67580. These compounds and their syntheses are described in C. Garret, et al., *Proceedings of the National Academy of Sciences (USA)*, 88:10208–10211 (1991) and the references cited therein.

Patent Cooperation Treaty publication WO 94/07843 describes a series of cyclohexylamiine derivatives typified by the following compound

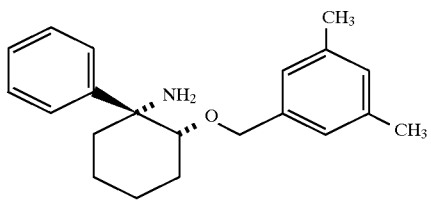

which are useful as tachykinin receptor antagonists.

Another group of compounds useful as tachykinin receptor antagonists is typified by the following compound.

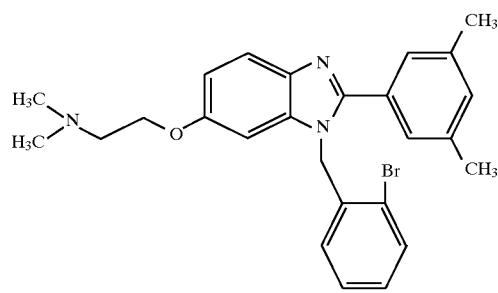

The synthesis of these compounds is described in European Patent Application Publication 694,535, published Jan. 31, 1996.

The compound (S)-1-(2-methoxybenzyl)-2-[(4-phenyl-1-piperazinyl)methyl]-4-(1H-indol-3-ylmethyl)-2-imidazoline and related compounds are described in European Patent Publication 699,665, published Mar. 6, 1996. This compound has the following structure.

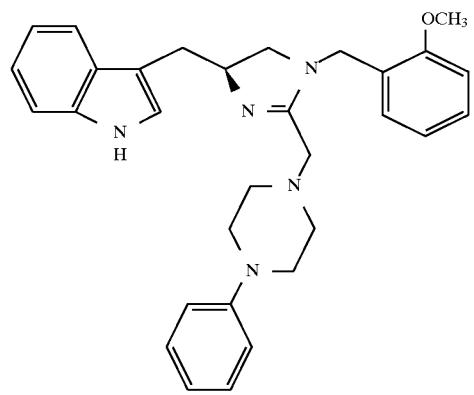

The above groups of compounds are only illustrative of the tachykinin receptor antagonists which are currently under development. This listing of groups of compounds is not meant to be comprehensive, the methods of the present invention may employ any tachykinin receptor antagonist and is not limited to any particular class of compound.

A most preferred class of tachykinin receptor antagonists are those compounds of the following structure

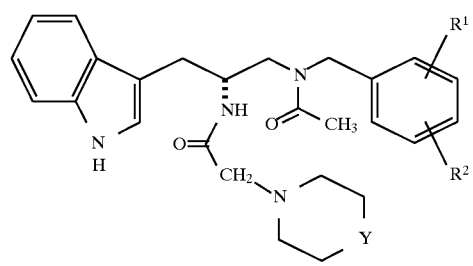

where $R^1$ and $R^2$ are independently selected from the group consisting of hydrogen, methyl, methoxy, chloro, and trifluoromethyl, with the proviso that no more than one of $R^1$ and $R^2$ can be hydrogen; and Y is

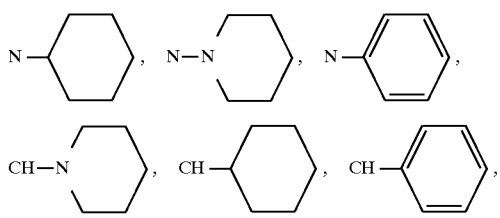

where $R^a$, $R^b$, and $R^c$ are independently selected from the group consisting of hydrogen and $C_1$–$C_6$ alkyl; or a pharmaceutically acceptable salt or solvate thereof. The syntheses of these compounds are described in Patent Cooperation Treaty Publications WO 95/14017, published May 26, 1995, and WO 96/01819, published Jan. 25, 1996. The syntheses of two typical compounds from this class are detailed infra.

Synthesis of (R)-2-[N-(2-((4-cyclohexyl)piperazin-1-yl)acetyl)amino]-3-(1H-indol-3-yl)-1-[N-(2-methoxybenzyl)acetylamino]propane

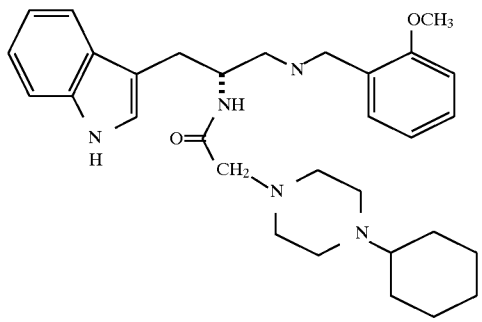

(a) Preparation of (R)-3-(1H-indol-3-yl)-2-(N-triphenylmethylamino)propanoic acid [N-trityltryptophan]

Tritylation

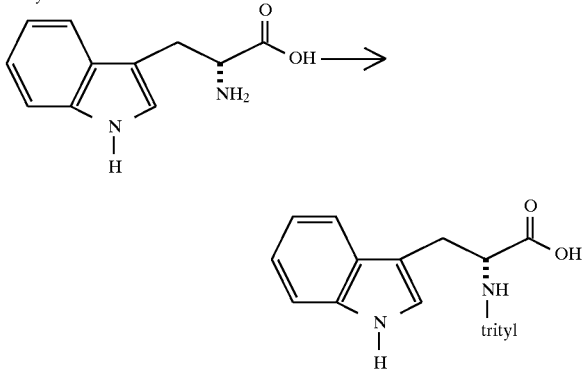

Chlorotrimethylsilane (70.0 ml, 0.527 mol) was added at a moderate rate to a stirred slurry of D-tryptophan (100.0 g, 0.490 mol) in anhydrous methylene chloride (800 ml) under a nitrogen atmosphere. This mixture was continuously stirred for 4.25 hours. Triethylamine (147.0 ml, 1.055 mol) was added, followed by the addition of a solution of triphenylmethyl chloride (147.0 g, 0.552 mol) in methylene chloride (400 ml) using an addition funnel. The mixture was stirred at room temperature, under a nitrogen atmosphere for at least 20 hours. The reaction was quenched by the addition of methanol (500 ml).

The solution was concentrated on a rotary evaporator to near dryness and the mixture was redissolved in methylene chloride and ethyl acetate. An aqueous work-up involving a 5% citric acid solution (2x) and brine (2x) was then performed. The organic layer was dried over anhydrous sodium sulfate, filtered, and concentrated to dryness on a rotary evaporator. The solid was dissolved in hot diethyl ether followed by the addition of hexanes to promote crystallization. By this process 173.6 g (0.389 mol) of analytically pure (R)-3-(1H-indol-3-yl)-2-(N-triphenylmethylamino)propanoic acid was isolated as a white solid in two crops giving a total of 79% yield.

FDMS 446 (M+).

$^1$H NMR (DMSO-$d_6$) δ 2.70 (m, 1H), 2.83 (m, 2H), 3.35 (m, 1H), 6.92–7.20 (m, 12H), 7.30–7.41 (m, 8H), 10.83 (s, 1H), 11.73 (br s, 1H).

Analysis for $C_{30}H_{26}N_2O_2$: Theory: C, 80.69; H, 5.87; N, 6.27. Found: C, 80.47; H, 5.92; N, 6.10.

(b) Preparation of (R)-3-(1H-indol-3-yl)-N-(2-methoxybenzyl)-2-(N-triphenylmethylamino)propanamide Coupling

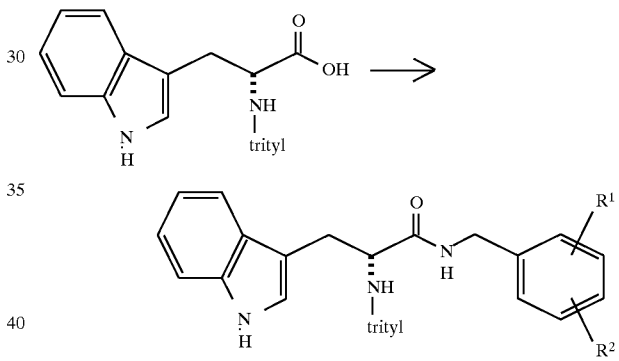

To a stirred solution of (R)-3-(1H-indol-3-yl)-2-(N-triphenylmethylamino)propanoic acid (179.8 g, 0.403 mol), 2-methoxybenzylamine (56.0 ml, 0.429 mol), and hydroxybenzotriazole hydrate (57.97 g, 0.429 mol) in anhydrous tetrahydrofuran (1.7 L) and anhydrous N,N-dimethylformamide (500 ml) under a nitrogen atmosphere at 0° C., were added triethylamine (60.0 ml, 0.430 mol) and 1-(3-dimethylaminopropyl)-3-ethoxycarbodiimide hydrochloride (82.25 g, 0.429 mol). The mixture was allowed to warm to room temperature under a nitrogen atmosphere for at least 20 hours. The mixture was concentrated on a rotary evaporator and then redissolved in methylene chloride and an aqueous work-up of 5% citric acid solution (2x), saturated sodium bicarbonate solution (2x), and brine (2x) was performed. The organic layer was dried over anhydrous sodium sulfate and concentrated to dryness on a rotary evaporator. The desired product was then recrystallized from hot ethyl acetate to yield 215.8 g (0.381 mol, 95%) of analytically pure material.

FDMS 565 (M+).

$^1$H NMR (CDCl$_3$) δ 2.19 (dd, J=6.4 Hz, Δν=14.4 Hz, 1H), 2.64 (d, J=6.5 Hz, 1H), 3.19 (dd, J=4.3 Hz, Δν=14.4 Hz, 1H), 3.49 (m, 1H), 3.63 (s, 3H), 3.99 (dd, J=5.4 Hz, Δν=14.2 Hz, 1H), 4.25 (dd, J=7.1 Hz, Δν=14.2 Hz, 1H), 6.64 (d,

J=2.1 Hz, 1H), 6.80 (d, J=8.2 Hz, 1H), 6.91 (t, J=7.4 Hz, 1H), 7.06–7.38 (m, 21 H), 7.49 (d, J=7.9 Hz, 1H), 7.75 (s, 1H).

Analysis for $C_{38}H_{35}N_3O_2$: Theory: C, 80.68; H, 6.24; N, 7.43. Found: C, 80.65; H, 6.46; N, 7.50.

(c) Preparation of (R)-3-(1H-indol-3-yl)-1-[N-(2-methoxybenzyl)amino]-2-(N-triphenylmethylamino) propane Reduction of Carbonyl

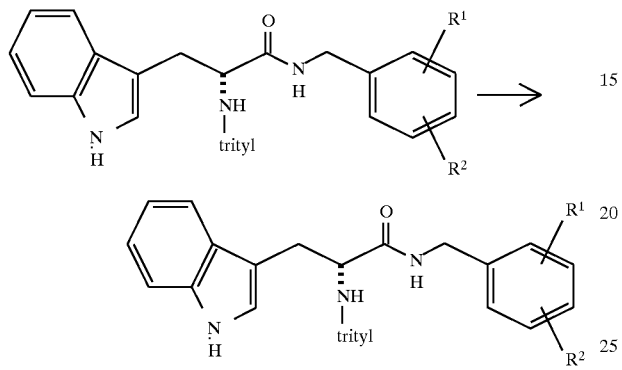

RED-AL®, [a 3.4M, solution of sodium bis(2-methoxyethoxy)aluminum hydride in toluene] (535 ml, 1.819 mol), dissolved in anhydrous tetrahydrofuran (400 ml) was slowly added using an addition funnel to a refluxing solution of the acylation product, (R)-3-(1H-indol-3-yl)-N-(2-methoxybenzyl)-2-(N-triphenylmethylamino) propanamide (228.6 g, 0.404 mols) produced supra, in anhydrous tetrahydrofuran (1.0 L) under a nitrogen atmosphere. The reaction mixture became a purple solution. The reaction was quenched after at least 20 hours by the slow addition of excess saturated Rochelle's salt solution (potassium sodium tartrate tetrahydrate). The organic layer was isolated, washed with brine (2×), dried over anhydrous sodium sulfate, filtered, and concentrated to an oil on a rotary evaporator. No further purification was done and the product was used directly in the next step.

(d) Preparation of (R)-3-(1H-indol-3-yl)-1-[N-(2-methoxybenzyl)-acetylamino]-2-(N-triphenylmethylamino)propane Acylation of Secondary Amine

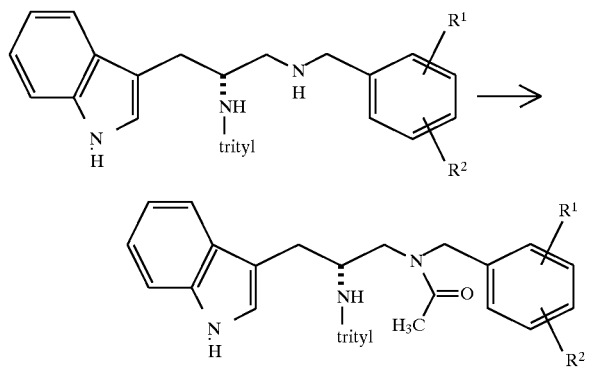

To a stirring solution of (R)-3-(1H-indol-3-yl)-1-[N-(2-methoxybenzyl)amino]-2-(N-triphenylmethylamino) propane (0.404 mol) in anhydrous tetrahydrofuran (1.2 L) under a nitrogen atmosphere at 0° C. was added triethylamine (66.5 ml, 0.477 mol) and acetic anhydride (45.0 ml, 0.477 mol). After 4 hours, the mixture was concentrated on a rotary evaporator, redissolved in methylene chloride and ethyl acetate, washed with water (2×) and brine (2×), dried over anhydrous sodium sulfate, filtered, and concentrated to a solid on a rotary evaporator. The resulting solid was dissolved in chloroform and loaded onto silica gel 60 (230–400 mesh) and eluted with a 1:1 mixture of ethyl acetate and hexanes. The product was then crystallized from an ethyl acetate/hexanes mixture. The resulting product of (R)-3-(1H-indol-3-yl)-1-[N-(2-methoxybenzyl) acetylamino]-2-(N-triphenylmethylamino)propane was crystallized and isolated over three crops giving 208.97 grams (87% yield) of analytically pure material.

Analysis for $C_{40}H_{39}N_3O_2$: Theory: C, 80.91; H, 6.62; N, 7.08. Found: C, 81.00; H, 6.69; N, 6.94.

(e) Preparation of (R)-2-amino-3-(1H-indol-3-yl)-1-[N-(2-methoxybenzyl)acetylamino]propane Deprotection

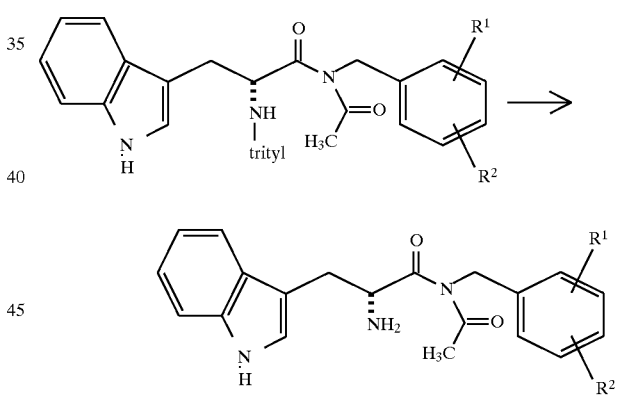

Formic acid (9.0 ml, 238.540 mmol) was added to a stirring solution of (R)-3-(1H-indol-3-yl)-1-[N-(2-methoxybenzyl)acetylamino]-2-(N-triphenylmethylamino) propane (14.11 g, 23.763 mmol) in anhydrous methylene chloride under a nitrogen atmosphere at 0° C. After 4 hours, the reaction mixture was concentrated to an oil on a rotary evaporator and redissolved in diethyl ether and 1.0N hydrochloric acid. The aqueous layer was washed twice with diethyl ether and basified with sodium hydroxide to a pH greater than 12. The product was extracted out with methylene chloride (4×). The organic extracts were combined, dried over anhydrous sodium sulfate, filtered, and concentrated on a rotary evaporator to a white foam. The compound (R)-2-amino-3-(1H-indol-3-yl)-1-[N-(2-methoxybenzyl) acetylamino]propane (7.52 g, 21.397 mmols) was isolated giving a 90% yield. No further purification was necessary.

(f) Preparation of (R)-2-amino-3-(1H-indol-3-yl)-1-[N-(2-methoxybenzyl)acetylamino]propane dihydrochloride

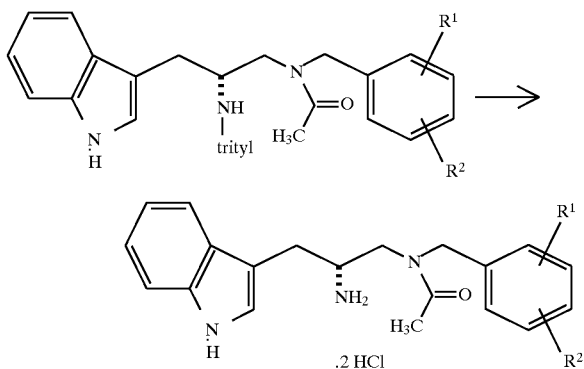

A stirring solution of (R)-3-(1H-indol-3-yl)-1-[N-(2-methoxybenzyl)acetylamino]-2-(N-triphenylmethylamino)propane in two volumes of methylene chloride was cooled to between −40° C. and −50° C.

Anhydrous hydrogen chloride gas was added at such a rate that the temperature of the reaction mixture did not exceed 0° C. The reaction mixture was stirred for 30 minutes to one hour at 0°–10° C.

To this reaction mixture was added two volumes of methyl t-butyl ether and the resulting mixture was allowed to stir for 30 minutes to one hour at 0°–10° C. The resulting crystalline solid was removed by filtration and then washed with methyl t-butyl ether. The reaction product was dried under vacuum at 50° C. (Yield>98%)

Analysis for $C_{21}H_{25}N_3O_2 \cdot 2$ HCl: Theory: C, 59.44; H, 6.41; N, 9.90. Found: C, 60.40; H, 6.60; N, 9.99.

(g) Preparation of 2-((4-cyclohexyl)piperazin-1-yl) acetic acid potassium salt hydrate Cyclohexylpiperazine (10.0 g, 0.059 mol) was added to ten volumes of methylene chloride at room temperature. To this mixture was added sodium hydroxide (36 ml of a 2N solution, 0.072 mol) and tetrabutylammonium bromide (1.3 g, 0.004 mol). After the addition of the sodium hydroxide and tetrabutylammonium bromide, methyl bromoacetate (7.0 ml, 0.073 mol) was added and the reaction mixture was stirred for four to six hours. The progress of the reaction was monitored by gas chromatography.

The organic fraction was separated and the aqueous phase was back-extracted with methylene chloride. The organic phases were combined and washed twice with deionized water, once with saturated sodium bicarbonate solution, and then with brine. The organic phase was dried over magnesium sulfate and the solvents were removed in vacuo to yield methyl 2-((4-cyclohexyl)piperazin-1-yl)acetate as a yellowish oil.

The title compound was prepared by dissolving the methyl 2-((4-cyclohexyl)piperazin-1-yl)acetate (10.0 g, 0.042 mol) in ten volumes of diethyl ether. This solution was cooled to 15° C. and then potassium trimethylsilanoate (5.9 g, 0.044) was added. This mixture was then stirred for four to six hours. The reaction product was removed by filtration, washed twice with five volumes of diethyl ether, then washed twice with five volumes of hexanes, and then dried in a vacuum oven for 12–24 hours at 50° C.

Analysis for $C_{12}H_{21}KN_2O_2 \cdot 1.5\ H_2O$: Theory: C, 49.63; H, 7.98; N, 9.65. Found: C, 49.54; H, 7.72; N, 9.11.

(h) Preparation of (R)-2-[N-(2-((4-cyclohexyl)piperazin-1-yl)acetyl)amino]-3-(1H-indol-3-yl)-1-[N-(2-methoxybenzyl)acetylamino]propane The title compound was prepared by first cooling 2-((4-cyclohexyl)piperazin-1-yl)acetic acid potassium salt to a temperature between −8° C. and −15° C. in 5 volumes of anhydrous methylene chloride To this mixture was added isobutylchloroformate at a rate such that the temperature did not exceed −8° C. The resulting reaction mixture was stirred for about 1 hour, the temperature being maintained between −8° C. and −15° C.

To this mixture was then added (R)-2-amino-3-(1H-indol-3-yl)-1-[N-(2-methoxybenzyl)acetylamino]propane dihydrochloride at such a rate that the temperature did not exceed 0° C. Next added to this mixture was N-methyl morpholine at a rate such that the temperature did not exceed 0° C. This mixture was then stirred for about 1 hour at a temperature between −15° C. and −8° C.

The reaction was quenched by the addition of 5 volumes of water. The organic layer was washed once with a saturated sodium bicarbonate solution. The organic phase was then dried over anhydrous potassium carbonate and filtered to remove the drying agent. To the filtrate was then added 2 equivalents of concentrated hydrochloric acid, followed by 1 volume of isopropyl alcohol. The methylene chloride was then exchanged with isopropyl alcohol under vacuum by distillation.

The final volume of isopropyl alcohol was then concentrated to three volumes by vacuum. The reaction mixture was cooled to 20° C. to 25° C. and the product was allowed to crystallize for at least one hour. The desired product was then recovered by filtration and washed with sufficient isopropyl alcohol to give a colorless filtrate. The crystal cake was then dried under vacuum at 50° C. MS 560 (M+1⁺).

$^1$H NMR (CDCl$_3$) δ 1.09–1.28 (m, 5H), 1.64 (d, J=10 Hz, 1H), 1.80–1.89 (m, 4H), 2.10 (s, 3H), 2.24–2.52 (m, 9H), 2.90 (s, 2H), 2.95 (d, J=7 Hz, 1H), 3.02 (d, J=7 Hz, 1H), 3.12 (dd, J=5, 14 Hz, 1H), 3.77 (s, 3H), 4.01 (dd, J=10, 14 Hz, 1H), 4.49 (ABq, J=17 Hz, 43 Hz, 2H), 4.56 (m, 1H), 6.79–6.87 (m, 3H), 7.05–7.24 (m, 4H), 7.34–7.41 (m, 2H), 7.67 (d, J=8 Hz, 1H), 8.22 (s, 1H).

Analysis for $C_{33}H_{45}N_5O_3$: Theory: C, 70.81; H, 8.10; N, 12.51. Found: C, 70.71; H, 8.21; N, 12.42.

Synthesis of (R)-3-(1H-indol-3-yl)-1-[N-(2-methoxybenzyl)acetylamino]-2-[N-(2-(4-piperidin-1-yl)piperidin-1-yl)acetyl)amino]propane

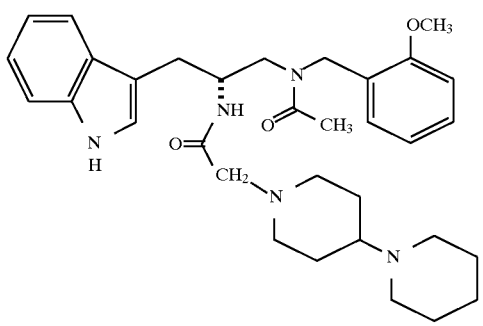

(a) Preparation of 2-(4-(piperidin-1-yl)piperidin-1-yl)acetic acid, potassium salt 4-(Piperidin-1-yl)piperidin (120 kg, 7.13 mol) was added to methylene chloride (12.0 L) under a nitrogen atmosphere.

Tetrabutylammonium bromide (0.150 kg, 0.47 mol) and sodium hydroxide (1.7 L of a 5N solution, 8.5 mol) were then added. The reaction mixture was cooled to 10°–15° C. and methyl bromoacetate (1.17 kg, 7.65 mol) was added and the resulting mixture was stirred for a minimum of 16 hours.

Deionized water (1.2 L) was then added to the mixture and the layers separated. The aqueous layer was back-extracted with methylene chloride (2.4 L). The organic fractions were combined and washed with deionized water (3×1.2 L), a saturated sodium bicarbonate solution (1.1 L) and a saturated sodium chloride solution (1.1 L). The organic fraction was then dried over anhydrous magnesium sulfate and concentrated to an oil on a rotary evaporator to yield 1.613 kg (93.5%) of methyl 2-(4-(piperidin-1-yl)piperidin-1-yl)acetate.

A solution of methyl 2-[4-(piperidin-1-yl)piperidin-1-yl]acetate (2.395 kg, 9.96 mol) in methanol (2.4 L) was added to a solution of potassium hydroxide (0.662 kg, 10.0 mol @ 85% purity) in methanol (10.5 L) under a nitrogen atmosphere. The reaction mixture was heated to 45°–50° C. for a minimum of 16 hours.

A solvent exchange from methanol to acetone (15.0 L) was performed on the solution on a rotary evaporator. This solution was slowly cooled to room temperature over 16 hours. The resulting solids were filtered, rinsed with acetone (5.0 L) and then dried to yield 2.471 kg (93.8%) of 2-(4-(piperidin-1-yl)piperidin-1-yl)acetic acid, potassium salt.

MS 265 ($M^{+1}$)

(b) Preparation of (R)-3-(1H-indol-3-yl)-1-[N-(2-methoxybenzyl)acetylamino]-2-[N-(2-(4-(piperidin-1-yl)piperidin-1-yl)acetyl)amino]propane The title compound was prepared by first admixing (R)-2-amino-3-(1H-indol-3-yl)-1-[N-(2-methoxybenzyl)acetylamino]propane dihydrochloride (50.0 g, 0.118 mol) with 100 ml of methylene chloride under a nitrogen atmosphere.

In a second flask, under a nitrogen atmosphere, 2-(4-(piperidin-1-yl)piperidin-1-yl)acetic acid potassium salt (62.3 g, 0.236 mol) was added to 600 ml of methylene chloride. This mixture was cooled to about −10° C. and stirring was continued. To this mixture isobutylchloroformate (23 ml, 0.177 mol) was added dropwise such that the temperature of the 2-(4-(piperidin-1-yl)piperidin-1-yl)acetic acid potassium salt mixture never rose appreciably.

This reaction mixture was stirred at about −10° C. for about 1.5 hours at which time the (R)-2-amino-3-(1H-indol-3-yl)-1-[N-(2-methoxybenzyl)acetylamino]propane dihydrochloride/methylene chloride mixture prepared supra was slowly added to the 2-(4-(piperidin-1-yl)piperidin-1-yl)acetic acid potassium salt/isobutylchloroformate/methylene chloride solution. The resulting mixture was then stirred for about 1 hour at a temperature between −15° C. and −8° C.

The reaction mixture was removed from the ice bath and allowed to warm to 15°–20° C. and the reaction was quenched by the addition of 200 ml of water. The pH of the solution was adjusted to 2.3–2.7 by the addition of 1N sulfuric acid. The layers were separated and the aqueous layer was washed with 100 ml of methylene chloride.

The organic fractions were combined and washed with water (100 ml). The water wash was back extracted with methylene chloride (50 ml) and combined with the aqueous fraction from above. Methylene chloride (500 ml) was added to the combined aqueous layers and the mixture was stirred at room temperature for 15 minutes as basification with 2N sodium hydroxide to a final pH of 9.8 to 10.2 was achieved.

The organic and aqueous fractions were separated. The aqueous fraction was washed with methylene chloride and the methylene chloride was added to the organic fraction. The organic fraction was then washed with a mixture of saturated sodium bicarbonate solution (100 ml) and water (50 ml). The bicarbonate wash was separated from the organic fraction and back extracted with methylene chloride (50 ml). The back extraction was combined with the methylene chloride fraction and the combined fractions were dried over magnesium sulfate. The magnesium sulfate was removed by filtration and the volatiles were removed by vacuum distillation to yield the title product as a foam. (72.5 g, >98% yield). MS 559($M^{+1}$)

NMR (MSO-$d_6$ 3:2 mixture of amide rotamers) δ 1.25–1.70 (m, 10H), 1.77–2.00 (m, 2H), 1.95 (s, ⅗.3H), 2.04 (s, ⅖.3H), 2.10–2.97 (m, 9H), 3.10–3.65 (m, 3H), 3.72 (s, ⅖.3H), 3.74 (s, ⅗.3H), 4.26–4.58 (m, 3H), 6.76–7.12 (m, 6H), 7.13–7.35 (m, 21), 7.42–7.66 (m, 2H), 10.80 (br s, 1H).

Analysis for $C_{33}H_{45}N_5O_3$: Theory: C, 70.81; H, 8.10; N, 12.51. Found: C, 70.57; H, 8.05; N, 12.39.

Preparation of (R)-3-(1H-indol-3-yl)-1-[N-(2-methoxybenzyl)acetylamino]-2-[N-(2-(4-(piperidin-1-yl)piperidin-1-yl)acetyl)amino]propane dihydrochloride trihydrate

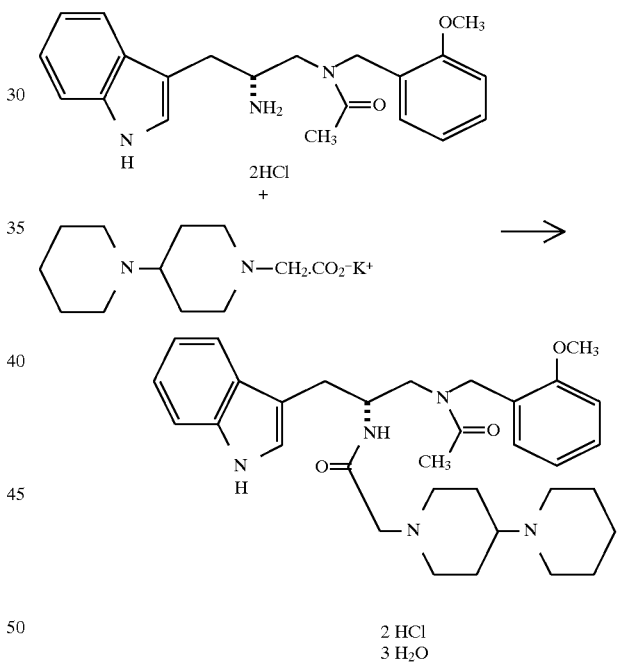

Under a nitrogen atmosphere 2-(4-(piperidin-1-yl)piperidin-1-yl)acetic acid, potassium salt (0.75 kg, 2.84 mol) was added to methylene chloride (7.5 L). The resulting mixture was cooled to −15° to −8° C. and isobutyl chloroformate (0.29 kg, 2.12 mol) was added at such a rate so as to maintain the temperature of the reaction mixture below −8° C. After the addition the resulting reaction mixture was stirred for 90 minutes between −15° and −8° C.

The reaction mixture was then cooled to −35° C. and solid (R)-2-amino-3-(1H-indol-3-yl)-1-[N-(2-methoxybenzyl)amino]propane dihydrochloride (0.60 kg, 1.14 mol) was added at such a rate that the reaction temperature was maintained at less than −20° C. After the addition, the reaction mixture was stirred for about one hour with the temperature being maintained between −37° C. and −20° C. The reaction was quenched by the addition of deionized water (7.5 L). The reaction mixture was basified to pH 12.8–13.2 by the addition of 5N sodium hydroxide. The aqueous fraction was removed and retained. Additional deionized water (3.75 L) was added to the organic fraction as was sufficient 5N sodium hydroxide to re-adjust the pH to 12.8–13.2.

The two aqueous fractions were combined, back-extracted with methylene chloride (1.5 L) and then discarded. The organic fractions were combined and washed with deionized water (4×3.5 L). These extracts were combined, back-extracted with methylene chloride (1.5 L), and then discarded. The two organic layers were combined and washed with a saturated sodium chloride solution (3.7 L).

The organic fraction was dried over anhydrous magnesium sulfate, filtered, and solvent exchanged from methylene chloride to acetone (3.75 L) on a rotary evaporator. An aqueous solution of hydrochloric acid (0.48 L of 6N solution, 2.88 mol) and seed crystals (2 g) were added and mixture was stirred for 30–90 minutes. Acetone (13.2 L) was then added and the slurry stirred for one hour. The resulting solid was then filtered, washed with acetone (2×1.4 L), and dried to yield 633 g (90%) of (R)-3-(1H-indol-3-yl)-1-[N-(2-methoxybenzyl)acetylamino]-2-[N-(2-(4-(piperidin-1-yl) piperidin-1-yl)acetyl)amino]propane dihydrochloride trihydrate.

The biological efficacy of a compound believed to be effective as a tachykinin receptor antagonist may be confirmed by employing an initial screening assay which rapidly and accurately measured the binding of the tested compound to known NK-1 and NK-2 receptor sites. Assays useful for evaluating tachykinin receptor antagonists are well known in the art. See. e.g., J. Jukic, et al., *Life Sciences*, 49:1463–1469 (1991); N. Kucharczyk, et al., *Journal of Medicinal Chemistry*, 36:1654–1661 (1993); N. Rouissi, et al., *Biochemical and Biophysical Research Communications*, 176:894–901 (1991).

NK-1 Receptor Binding Assay

Radioreceptor binding assays were performed using a derivative of a previously published protocol. D. G. Payan, et al., *Journal of Immunology*, 133:3260–3265 (1984). In this assay an aliquot of IM9 cells (1×10$^6$ cells/tube in RPMI 1604 medium supplemented with 10% fetal calf serum) was incubated with 20 pM $^{125}$I-labeled substance P in the presence of increasing competitor concentrations for 45 minutes at 4° C.

The IM9 cell line is a well-characterized cell line which is readily available to the public. See, e.g., *Annals of the New York Academy of Science*, 190:221–234 (1972); *Nature (London)*, 251:443–444 (1974); *Proceedings of the National Academy of Sciences (USA)*, 71:84–88 (1974). These cells were routinely cultured in RPMI 1640 supplemented with 50 μg/ml gentamicin sulfate and 10% fetal calf serum.

The reaction was terminated by filtration through a glass fiber filter harvesting system using filters previously soaked for 20 minutes in 0.1% polyethylenimine. Specific binding of labeled substance P was determined in the presence of 20 nM unlabeled ligand.

Many of the compounds employed in the methods of the present invention are also effective antagonists of the NK-2 receptor.

NK-2 Receptor Binding Assay

The CHO-hNK-2R cells, a CHO-derived cell line transformed with the human NK-2 receptor, expressing about 400,000 such receptors per cell, were grown in 75 cm$^2$ flasks or roller bottles in minimal essential medium (alpha modification) with 10% fetal bovine serum. The gene sequence of the human NK-2 receptor is given in N. P. Gerard, et al., *Journal of Biological Chemistry*, 265:20455–20462 (1990).

For preparation of membranes, 30 confluent roller bottle cultures were dissociated by washing each roller bottle with 10 ml of Dulbecco's phosphate buffered saline (PBS) without calcium and magnesium, followed by addition of 10 ml of enzyme-free cell dissociation solution PBS-based, from Specialty Media, Inc.). After an additional 15 minutes, the dissociated cells were pooled and centrifuged at 1,000 RPM for 10 minutes in a clinical centrifuge. Membranes were prepared by homogenization of the cell pellets in 300 ml 50 mM Tris buffer, pH 7.4 with a Tekmar® homogenizer for 10–15 seconds, followed by centrifugation at 12,000 RPM (20,000×g) for 30 minutes using a Beckman JA-14® rotor. The pellets were washed once using the above procedure. and the final pellets were resuspended in 100–120 ml 50 mM Tris buffer, pH 7.4, and 4 ml aliquots stored frozen at −70° C. The protein concentration of this preparation was 2 mg/ml.

For the receptor binding assay, one 4-ml aliquot of the CHO-hNK-2R membrane preparation was suspended in 40 ml of assay buffer containing 50 mM Tris, pH 7.4, 3 mM manganese chloride, 0.02% bovine serum albumin (BSA) and 4 μg/ml chymostatin. A 200 μl volume of the homogenate (40 μg protein) was used per sample. The radioactive ligand was [$^{125}$I]iodohistidyl-neurokinin A (New England Nuclear, NEX-252), 2200 Ci/mmol. The ligand was prepared in assay buffer at 20 nCi per 100 μl; the final concentration in the assay was 20 pM. Non-specific binding was determined using 1 μM eledoisin. Ten concentrations of eledoisin from 0.1 to 1000 nM were used for a standard concentration-response curve.

All samples and standards were added to the incubation in 10 μl dimethylsulfoxide (DMSO) for screening (single dose) or in 5 μl DMSO for IC$_{50}$ determinations. The order of additions for incubation was 190 or 195 μl assay buffer, 200 μl homogenate, 10 or 5 μl sample in DMSO, 100 μl radioactive ligand. The samples were incubated 1 hr at room temperature and then filtered on a cell harvester through filters which had been presoaked for two hours in 50 mM Tris buffer, pH 7.7, containing 0.5% BSA. The filter was washed 3 times with approximately 3 ml of cold 50 mM Tris buffer, pH 7.7. The filter circles were then punched into 12×75 mm polystyrene tubes and counted in a gamma counter.

Upon a showing that a compound has activity as a tachykinin receptor antagonist, assays may be used to demonstrate the ability of such a compound to control or treat hypertension. Typical such assays are described below.

In Vivo Assays

Assay 1

The procedure as set out in Farhat, et al., *J PET*, 261: 686 (1992) (herein incorporated by reference) is carried out. Four to thirty rats are sacrificed. The lungs are exsanguinated by perfusion via the hepatic pulmonary vein. The pulmonary artery is cannulated as is the trachea to maintain ventilation and the pulmonary cannula is connected to the perfusion line and the whole ventilated lung is removed and suspended in a perfusion chamber. The effects of vasoconstrictor substances on perfusion pressure of the isolated perfused lung is measured using a Statham pressure transducer. The increase in perfusion pressure (vasoconstriction) induced by thromboxane mimetics in the presence of estradiol is determined and the ability to block the thromboxane effects with a first compound or the estradiol potentiation of the thromboxane effects will be determined.

Activity of compounds having activity as tachykinin receptor antagonists is illustrated by a reduction in pulmonary perfusion pressure increase following thromboxane mimetic stimulation.

Assay 2

Between five and fifty rats are administered a single IV dose of monocrotaline pyrrole (3.5 mg/kg) and pulmonary disease is evaluated by histopathology, accumulation of fluorescein conjugated dextran in bronchial alveolar lavage fluid (as a measurement of pulmonary edema), and measurements of pulmonary artery pressure using a Standtham P23ID pressure transducer (Reindel et al., Tox and Applid. Pharm, 106: 179–200 (1990), incorporated herein by reference. A test compound is administered and the effect on the rats are evaluated.

Activity of compounds having activity as tachykinin receptor antagonists is illustrated by a reduction in uptake of fluorescein conjugated dextran from bronchial alveolar lavage fluids of animals treated with a compound of formula 1, indicating a reduction in pulmonary edema. Rat lungs will also be removed from thorax, perfused with modified Karnovskys fixitive and processed for histopathology. A reduction in thickening of the arterial walls in treated rats is evidence for the protective role of compounds of formula 1 as is a decrease in pulmonary artery pressure.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Preparation 1

Hard gelatin capsules containing the following ingredients are prepared:

| Ingredient | Quantity (mg/capsule) |
| --- | --- |
| Active Ingredient(s) | 30.0 |
| Starch | 305.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/tablet) |
| --- | --- |
| Active Ingredient(s) | 25.0 |
| Cellulose, microcrystalline | 200.0 |
| Colloidal silicon dioxide | 10.0 |
| Stearic acid 5.0 | |

The components are blended and compressed to form tablets, each weighing 240 mg.

Formulation Preparation 3

A dry powder inhaler formulation is prepared containing the following components:

| Ingredient | Weight % |
|---|---|
| Active Ingredient(s) | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/tablet) |
|---|---|
| Active Ingredient(s) | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
|---|---|
| Active Ingredient(s) | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 25 mg of active ingredient are made as follows:

| Ingredient | Amount |
|---|---|
| Active Ingredient(s) | 25 mg |
| Saturated fatty acid glycerides to | 2,000 mg |

The active ingredient(s) is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
|---|---|
| Active Ingredient(s) | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Quantity (mg/capsule) |
|---|---|
| Active Ingredient(s) | 15.0 mg |
| Starch | 407.0 mg |
| Magnesium stearate | 3.0 mg |
| Total | 425.0 mg |

The active ingredient(s), cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
|---|---|
| Active Ingredient(s) | 250.0 mg |
| Isotonic saline | 1000 ml |

Formulation Preparation 10

A topical formulation may be prepared as follows:

| Ingredient | Quantity |
| --- | --- |
| Active Ingredient(s) | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
| --- | --- |
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:

1. A method of inhibiting pulmonary hypertensive disease in a mammal which comprises administering to a mammal in need thereof an effective amount of a compound or composition having activity as a tachykinin receptor antagonist.

2. A method as claimed in claim 1 wherein the compound having activity as a tachykinin receptor antagonist is (R)-2-[N-(2-((4-cyclohexyl)piperazin-1-yl)acetyl)amino]-3-(1H-indol-3-yl)-1-[-(2-methoxybenzyl)acetylamino] propane, (R)-3-(1H-indol-3-yl)-1-[N-(2-methoxybenzyl) acetylamino]-2-[N-(2-(4-(piperidin-1-yl)piperidin-1-yl) acetyl)amino]propane, (R)-3-(1H-indol-3-yl)-1-[N-(2-methoxybenzyl)acetylamino]-2-[N-(2-(4-(piperidin-1-yl) piperidin-1-yl)acetyl)amino]propane dihydrochloride trihydrate, 1-(2-bromobenzyl)-2-(3,5-dimethylphenyl)-6-[2-(N,N-dimethylamino)ethoxy]benzimidazole, RP 67580, (±)CP 96345, 5-(3,5-bistrifluoromethylphenyl)-1-(3-indolyl)-2-((4-methylpiperazin-1-yl)acetamido)-3-pentanone, (4-methylphenyl)methyl [R-(R*,S*)]-[1-(1H-indol-3-ylmethyl)-1-methyl-2-oxo-2-[(1-phenylethyl) amino]ethyl]carbamate, or 1-(3,5-dimethylbenzyloxy)-2-amino-2-phenylcyclohexane, or a salt or solvate thereof.

* * * * *